US00PP33080P2

(12) United States Plant Patent
Hansen

(10) Patent No.: US PP33,080 P2
(45) Date of Patent: May 18, 2021

(54) ***X MANGAVE* PLANT NAMED 'BRIDAL FALLS'**

(50) Latin Name: ***Manfreda* times *Agave*, X *Mangave***
Varietal Denomination: Bridal Falls

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/974,102

(22) Filed: Sep. 30, 2020

(51) Int. Cl.
*A01H 5/12* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./373
CPC ..... A01H 6/12
See application file for complete search history.

*Primary Examiner* — Anne Marie Grunberg

(57) ABSTRACT

A new and unique x *Mangave* plant named 'Bridal Falls' characterized by a medium mound of broad, fleshy, longitudinally folded, medium green foliage having a broad creamy-white margin and minty-green intermediate zone. The leaves cascade or arch downward toward the apices. Foliage displays faint spots that in low ultraviolet light are dark green in the leaf centers or purplish-pink in the margins. The new plant is suitable for the garden or as a potted plant in the garden or home.

1 Drawing Sheet

Botanical classification: Hybrid; *Manfreda* times *Agave*, known as x *Mangave*.

Variety denomination: 'Bridal Falls'.

BACKGROUND OF THE INVENTION

The present invention relates to the new and distinct x *Mangave* hybrid plant, x *Mangave* 'Bridal Falls' discovered by the inventor at a wholesale perennial nursery in Zeeland, Mich., USA as an uninduced whole plant mutation of x *Mangave* 'Falling Waters' U.S. Plant Pat. No. 30,650 on Oct. 4, 2019. Through trials at the same nursery the plant was assigned the breeder code 19-SP-MANG-895. The new plant has been successfully asexually propagated by sterile shoot-tip tissue culture at the same nursery in Zeeland, Mich. and been found to produce stable and identical plants that maintain all the unique characteristics of the original plant.

No plants of x *Mangave* 'Bridal Falls' have been sold, under this or any name, in this country or anywhere in the world, prior to the filing of this application, nor has any disclosure of the new plant been made prior to the filing of this application.

BRIEF SUMMARY OF THE INVENTION

X *Mangave* 'Bridal Falls' differs from its parent as well as all other *Manfreda, Agave* and x *Mangave* known to the applicant. The new plant has habit and foliage that is similar, but the leaves of the new plant have a wide, contrasting, creamy-white margin and distinctive minty green intermediate zone between the creamy-white margin and the medium green leaf center. The nearest comparison plant is x *Mangave* 'Foxy Lady' U.S. Plant patent application Ser. No. 16/602,783. 'Navajo Princess' U.S. Plant Pat. No. 31,136 and 'Snow Leopard' U.S. Plant Pat. No. 31,137 are both variegated with creamy-white margins but the foliage is longer, flatter and with smaller marginal teeth. 'Pineapple Punch' U.S. Plant Pat. No. 32,041 and 'Kaleidoscope' U.S. Plant Pat. No. 28,614 both have variegated margins, but differ in the margins being yellowish and the foliage is narrower with smaller teeth and more intense spotting. 'Pineapple Punch' has shorter leaves while 'Kaleidoscope' has longer leaves. The foliage of 'Foxy Lady' is flatter and more glaucous, producing a silvery color with more lavender undertones, and the marginal teeth have stiffer apices that develop to an orangish-brown coloration. 'Falling Waters' differs in not having the creamy-white margin and the minty-green intermediate zone between the margin and the leaf center.

The new plant, 'Bridal Falls', is unique from all of the above listed cultivars and all *Agave*, x *Mangave* and *Manfreda* known to the inventor by the following combined traits:

1. Medium mound of medium green lanceolate, broad, fleshy, longitudinally folded foliage;
2. Leaf margins are creamy-white with a minty-green between the margin and the leaf center;
3. Foliage has faint spots that become more pronounced mahogany-colored in strong ultraviolet light;
4. Leaf margins deeply scalloped with small teeth;
5. Moderate growth rate.
6. Foliage cascades or arches with age.

BRIEF DESCRIPTION OF THE DRAWING

The photograph of x *Mangave* 'Bridal Falls' demonstrates the overall appearance of the new plant including the unique traits as a one-year-old plant grown in a container in a greenhouse with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
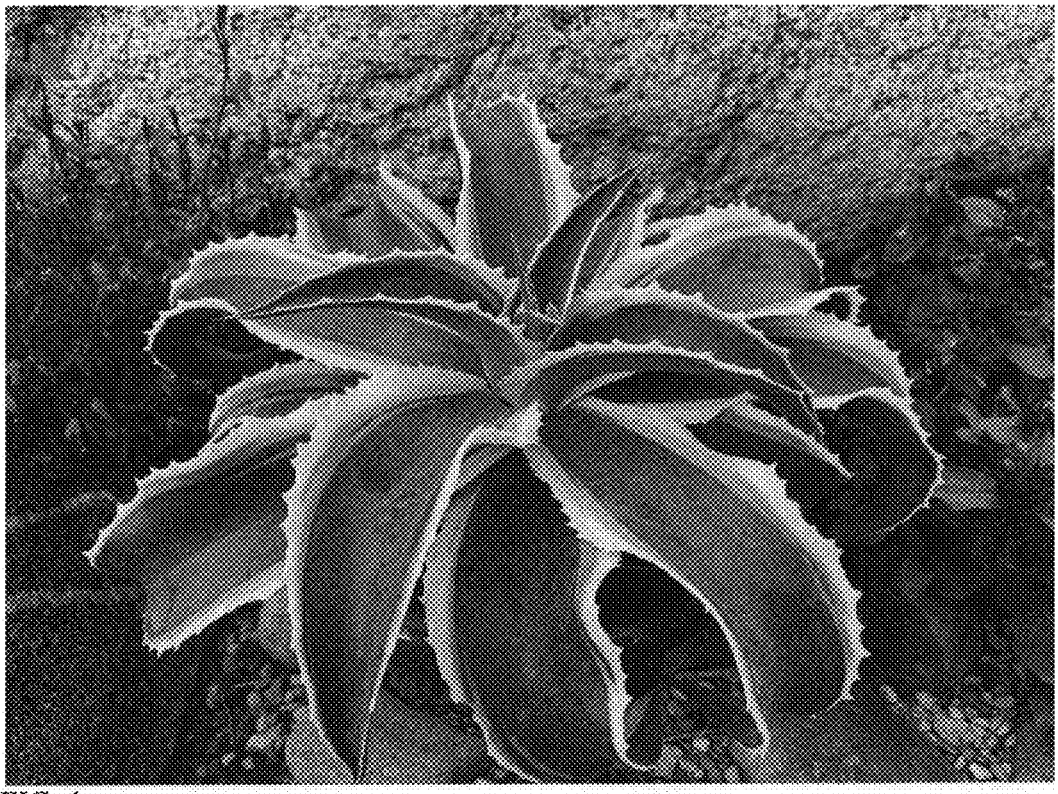
FIG. 1 shows the habit of the new plant from a side angle.
Figure 2:
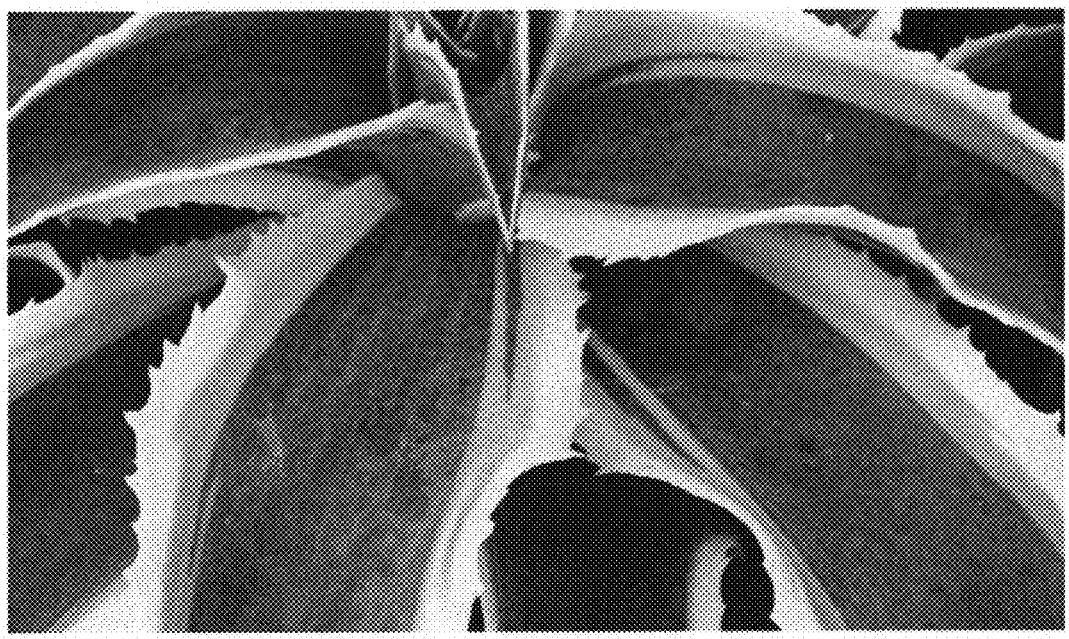
FIG. 2 shows a close-up of the variegation of the leaves and the marginal teeth.

The following descriptions and color references are based on the 2015 edition of The Royal Horticultural Society Colour Chart except where common dictionary terms are used. The new plant, x *Mangave* 'Bridal Falls', has not been observed under all possible environments. The phenotype may vary slightly with different environmental conditions, such as temperature, light, fertility, moisture and maturity levels, but without any change in the genotype. The following observations and size descriptions are of a one-year old plant in a partially-shaded, commercial, wholesale greenhouse in Zeeland, Mich. with supplemental water and fertilizer as needed.

Parentage: An uninduced mutation of x *Mangave* 'Falling Waters' as the sport parent;

Propagation: By sterile shoot-tip tissue culture;

Time to initiate roots from tissue culture: About 21 days;

Growth rate: Moderate;

Crop time: About 12 to 16 weeks to finish in a 3.8 liter container from a 35 mm tissue culture growing at about 21° C.;

Rooting habit: Fleshy, lightly branching, with roots up to 18 cm long;

Root color: Nearest RHS 158C;

Plant shape and habit: Succulent herbaceous perennial with basal rosettes of about 18 leaves radially emerging outwardly from central stem, producing a radially-symmetrical, rounded mound;

Plant size: Foliage height about 38.0 cm tall from soil line to the top of the leaves and about 33.0 cm wide at the widest point slightly below soil line in container;

Foliage description: Lanceolate; simple; sessile; bi-laterally symmetrical; apex acute with apical spine; apical spine to about 5.0 mm long; base truncate; conduplicate, especially young distal leaves; margins coarsely irregularly dentate; slightly glaucous waxy bloom abaxial and adaxial; without trichomes; with abaxial and adaxial spots about 2.0 mm to 3.0 mm long and wide rarely touching or overlapping;

Teeth: Sharp; initially flexible, becoming harder with age; about 1.0 mm long and 1.0 mm long on end of protrusion to about 4.0 mm long and about 4.0 mm wide at base; protrusions average about 8.0 mm apart on mature leaves;

Leaf size: To about 23.5 cm long, about 7.0 cm wide toward base; and about 5.0 mm thick at base; average about 20.0 cm long, 5.5 cm wide and 4.0 mm thick; adaxial and abaxial margin to about 12.0 mm wide, center to about 4.5 cm wide and intermediate zone to about 8.0 mm wide; abaxial margin to about 8.0 mm wide;

Foliage fragrance: None observed;

Leaf number: About 20 per plant;

Leaf blade color:

*Adaxial* (*young*).—Center nearest RHS N138B with spots nearest RHS 137A in low ultraviolet light; margin and marginal teeth between RHS 8D and RHS 11D with spots nearest RHS 186C; intermediate zone between margin and center between RHS N138D and RHS 189B.

*Abaxial* (*young*).—Center nearest RHS N138B with spots nearest RHS 137B; margin and marginal teeth between RHS 8D and RHS 11D with spots nearest RHS 186C; intermediate zone variable in longitudinal streaks between RHS N138D and RHS 189B in some portions and nearest RHS 141D in others with spots not obvious.

*Adaxial* (*older*).—Center nearest RHS 138B with spots nearest RHS 137A; margin and teeth between RHS NN155D and RHS NN155C and spots not obvious; intermediate zone between RHS N138D and RHS 189B with spots not obvious.

*Abaxial* (*older*).—Center nearest RHS N138B with spots nearest RHS 137B; margin and teeth nearest RHS NN155C with spots not obvious; intermediate zone between RHS N138D and RHS 189B with spots not obvious.

*Apical spine*.—On young leaves nearest RHS 166B and on older leaves to nearest RHS 166A. Adaxial and abaxial also occasionally displaying random streaks with the margin color breaching into the center or intermediate zone and from the center breaching into the margin or intermediate zone.

Petiole: Leaves sessile;

Veins: Parallel; not distinct abaxial or adaxial;

Flower description: Not yet observed to date;

Fruit and seed not observed to date;

Disease resistance: X *Mangave* 'Bridal Falls' has not been observed to be resistant to diseases beyond that which is normal for x *Mangave, Agave* or *Manfreda*. The new plant is xeromorphic and survives well with minimal water once established. The new plant is estimated to be hardy at least from USDA zone 7b. Full extent of winter hardiness has not been tested.

It is claimed:

1. A new and distinct cultivar of ornamental x *Mangave* plant named 'Bridal Falls' as herein described and illustrated.

* * * * *